(12) United States Patent
Hall et al.

(10) Patent No.: US 10,918,362 B2
(45) Date of Patent: Feb. 16, 2021

(54) TOILET VOLATILE ORGANIC COMPOUND ANALYSIS SYSTEM FOR URINE

(71) Applicants: David R. Hall, Provo, UT (US); Dan Allen, Springville, UT (US); Steven Butala, Provo, UT (US); Ben Swenson, Lehi, UT (US); Gayun Kim, Provo, UT (US); Joshua Larsen, Spanish Fork, UT (US); Jared Reynolds, Pleasant Grove, UT (US); Joe Fox, Spanish Fork, UT (US); Cameron Price, Provo, UT (US)

(72) Inventors: David R. Hall, Provo, UT (US); Dan Allen, Springville, UT (US); Steven Butala, Provo, UT (US); Ben Swenson, Lehi, UT (US); Gayun Kim, Provo, UT (US); Joshua Larsen, Spanish Fork, UT (US); Jared Reynolds, Pleasant Grove, UT (US); Joe Fox, Spanish Fork, UT (US); Cameron Price, Provo, UT (US)

(73) Assignee: Hall Labs LLC, Provo, UT (US)

( * ) Notice: Subject to any disclaimer, the term of this patent is extended or adjusted under 35 U.S.C. 154(b) by 998 days.

(21) Appl. No.: 15/250,039

(22) Filed: Aug. 29, 2016

(65) Prior Publication Data
US 2018/0055488 A1 Mar. 1, 2018

(51) Int. Cl.
*A61B 10/00* (2006.01)
*E03D 11/11* (2006.01)
*G01N 33/493* (2006.01)
*A61B 5/00* (2006.01)
*G01N 1/40* (2006.01)
*A61B 5/20* (2006.01)
*E03D 11/13* (2006.01)

(52) U.S. Cl.
CPC .......... *A61B 10/007* (2013.01); *A61B 5/0022* (2013.01); *A61B 5/207* (2013.01); *E03D 11/11* (2013.01); *G01N 1/405* (2013.01); *G01N 33/493* (2013.01); *E03D 11/13* (2013.01); *E03D 2201/00* (2013.01)

(58) Field of Classification Search
CPC ..... A61B 10/007; A61B 5/207; A61B 5/0022; G01N 1/405; G01N 33/493; E03D 11/11
See application file for complete search history.

(56) References Cited

U.S. PATENT DOCUMENTS 4,003,257 A * 1/1977 Fletcher ................. G01N 30/06
73/19.02
4,315,890 A * 2/1982 Tamers ................. B01L 3/0217
422/401

(Continued)

FOREIGN PATENT DOCUMENTS

JP 2009062739 A * 3/2009

*Primary Examiner* — Daniel L Cerioni (57) ABSTRACT

An in-toilet urine sampling and measurement system is disclosed. One or more toilet sensors trigger volatilization, measurement, and analysis of volatile compounds in a urine sample. Volatile urine compounds may be concentrated, measured, and analyzed by a measurement system attached to a toilet bowl. A volatilizer system may use heat generated from one or more measurement devices to assist in volatilization of the urine sample.

19 Claims, 10 Drawing Sheets

(56) References Cited

U.S. PATENT DOCUMENTS

| | | | | |
|---|---|---|---|---|
| 4,631,061 | A * | 12/1986 | Martin | A61F 5/44 604/318 |
| 4,735,777 | A * | 4/1988 | Mitsui | A61B 5/083 422/70 |
| 4,961,431 | A * | 10/1990 | Ikenaga | A61B 5/14507 600/573 |
| 5,730,149 | A * | 3/1998 | Nakayama | G01N 1/12 600/573 |
| 2013/0346091 | A1* | 12/2013 | Margon | G06F 19/3418 705/2 |
| 2015/0164292 | A1* | 6/2015 | Shin-Ya | G06F 19/3418 705/2 |
| 2015/0289782 | A1* | 10/2015 | Peverall | A61B 5/14532 600/532 |
| 2016/0097751 | A1* | 4/2016 | Dron | A61B 5/083 422/70 |
| 2016/0161459 | A1* | 6/2016 | Rouse | G01N 1/28 73/31.07 |
| 2018/0052955 | A1* | 2/2018 | Hall | A61B 5/0022 |
| 2018/0184906 | A1* | 7/2018 | Prokopp | A61B 5/0022 |

* cited by examiner

TOILET VOLATILE ORGANIC COMPOUND ANALYSIS SYSTEM FOR URINE

BACKGROUND

Field of the Invention

The present invention relates to the collection and analysis of urine samples.

Background of the Invention

Chromatographic analysis of human urine can provide diagnostic indicators of gastrointestinal and other bodily disorders. Currently, samples are typically taken from a patient and stored until laboratory analysis, and the analytical procedure itself usually entails the use of large and sometimes sophisticated instrumentation. Typically, a hospital or lab has a large machine with a liquid handling robotic system that drips sample urine into several cuvettes with color change reagents, mixes, incubates and then measures the color with a spectrophotometer. Other methods use color change reagents embedded into paper. The color change strips are dipped in urine and compared to a chart, providing only semi-quantitative results. More sophisticated analytical systems include (e.g., gas chromatography (GC), gas chromatography with mass spectrometry (GC/MS), solid phase micro-extraction with gas chromatography (SPME/GC), etc. These systems often require considerable maintenance. Furthermore, shelf life of samples, even under refrigerated conditions, can be severely limited.

An automated analytical methodology with small instrumentation as part of the toilet itself, would therefore, be highly desirable. Some chemicals in high concentrations can be quantified by spectroscopy, such as urea, creatinine and glucose. However, chemicals in low concentrations are difficult to measure by spectroscopy since their absorption is very small and can be masked by the water absorption features. Among chemicals of low concentration are ketone bodies which are products of ketoacidosis, a metabolic function indicative of either a lack of blood sugar or non-functional insulin. High ketone bodies are indicative of an untreated diabetic condition when the urinary sugar level is high. Another chemical of interest is ethanol, a molecule only present in the urine if ingested. A simple measurement of the total volatile organic compound (VOC) concentration in urine would include contributions from ketones, ethanol and for some sensors potentially contributions from ammonia, a byproduct of bacterial action in urine. What is needed is a way to separately measure volatile compounds in urine at low concentration in a convenient manner.

SUMMARY

This invention has been developed in response to the present state of the art and, in particular, in response to the problems and needs in the art that have not yet been fully solved by currently available systems and methods. Accordingly, an in-toilet sampling and measurement system has been developed. Features and advantages of different embodiments of the invention will become more fully apparent from the following description and appended claims, or may be learned by practice of the invention as set forth hereinafter.

An in-toilet sampling and measurement system is disclosed. One or more toilet sensors trigger measurement and analysis of a urine sample. A volatilizer system may use heat generated from on optical measurement system or microprocessor to assist in volatilization of the urine sample. A volatilizer system may comprise one or more of: a bubbler, a heater, a light source heater, a gas-permeable sorbent material, a vacuum generator, a stirring device, or a combination thereof. A urine sample may be kept at a raised temperature higher than an ambient temperature of the toilet to assist in obtaining and measuring volatile organic compounds (VOCs) in the urine. A urine sample may be heated between 90 to 200 degrees Fahrenheit while VOCs are collected from the urine sample. An additional heater may be used to heat a concentrator to release concentrated volatile organic compounds stored in the concentrator.

A single sensor or a combination of sensors may be used to trigger measurement and analysis of a urine sample. Trigger sensor may include: a temperature sensor, a thermal imaging sensor, an optical sensor, an infrared sensor, a motion sensor, an acoustic sensor, a pH sensor, and/or a gas sensor. In an example the trigger is a temperature sensor which detects urination. In another example the triggering device is a scale or motion detector for detecting the presence of a user. In another example the triggering device is a flow or level sensor in the toilet bowl or P-trap. In another example the triggering device is a wireless connection to a user personal electronic device or a button on a remote control or personal electronic device. In another example the triggering device is a thermal imaging system, optical camera system, infrared detector, motion detector, acoustic sensor or gas sensor. A triggering sensor may trigger a temperature of a urine capture device to heat to a predetermined value before receiving urine preventing the urine from cooling down due to an ambient temperature of the toilet. Once a urine sample is received, the temperature may be raised to help release VOCs. Urine may then be kept at a constant or ramping temperature while VOCs are released and measured.

Sample collection begins with a mechanism for collecting urine within a receptacle within a bowl of a toilet. The receptacle may have one or more temperature sensors built-in or in direct contact with a receptacle surface and/or a urine surface. A urine sample is collected as a toilet user urinates in the toilet. The urine may be received directly into a receptacle in the toilet bowl or may be received by indirect contact after running down an inner surface of the toilet bowl. In an example a depression, slit, or receptacle within the toilet bowl collects a urine sample and is accessed by a port or drain. In another example the urine is collected on a sorbent material, such as a sponge. In another example the urine is captured in a capillary, a slot or other surface tension-based liquid capture feature. The urine sample is then volatized and can be introduced directly into a liquid or gas chromatography column or electrophoresis column. A vacuum generator may be used in connection with a heated micro-capillary or heated surface-tension-based-system to decrease atmospheric pressure to effectively pull VOC gas molecules directly into a gas column.

Volatilization occurs by means of a volatilizer system, used in this context to indicate a device or devices that are capable of individually or collectively volatilizing a sample. A volatilizer may achieve volatilization of the urine by pulling vacuum on a captured liquid sample, blowing heated air through a sample in a porous medium or sorbent medium such as a sponge, or paper, directly heating the urine, or a combination thereof. The heated air may be heated by a light source of an optical system which measures the VOCs in the volatized sample. Heated air may be generated by blowing air across a light source directly or through a heat exchange system used to cool the light source. In an example, volatizing the urine is accomplished by bubbling air, heated air, or another gas through the urine to capture and extract VOCs. VOCs readily dissolve into heated air or are released due to a temperature change in a urine sample as a result of being heated. An optical system of a measurement device may provide heat to assist in the volatilization process of a received sample. For instance, gas or air may be heated by a measurement light source and then bubbled through a received sample. Heated gas or air may be blown across a micro-capillary tube or a urine sample receptacle to assist in releasing VOCs in the urine. Additionally, or alternatively, a received sample may be heated by a light source of a measurement system used to measure VOCs of the received sample after and during volatilization of the sample. A VOC heat curve may be used to detect, quantify, and identify VOCs.

VOCs extracted from the urine in a gas phase may then be collected onto a concentrator or pre-concentrator. In an example, the concentrator includes a concentrating media such as activated charcoal or molecular sieve. In another example the concentrator is a polymer.

The concentrated sample can then be measured, or VOCs extracted from the concentrator for further measuring and processing. Extracting concentrated VOCs may include heating the concentrator or pre-concentrator to temperatures between 90 and 700 degrees Fahrenheit using an inductive heater.

Consistent with the foregoing, an in-toilet urinalysis system is disclosed. In various embodiments a button, strain sensor, pH probe, optical sensor or other trigger is used to start a VOC volatilization and detection process. In various embodiments of the in-toilet urinalysis system the volatilizer system comprises one or more of: a bubbler, a heater, a light source heater, a vacuum generator, or gas-permeable sorbent material. In various embodiments one or more measurement devices comprises a metal oxide sensor, a mass spectrometer, a processor, a wireless transmitter, and software necessary to digitally process and digitally filter sensor data. The in-toilet urinalysis system is shown in several embodiments with a column separator that may operate by means of gas chromatography, liquid chromatography, or electrophoresis. The in-toilet urinalysis system is also shown in several embodiments without said column separator. Further varieties and embodiments of an in-toilet urinalysis system are disclosed.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
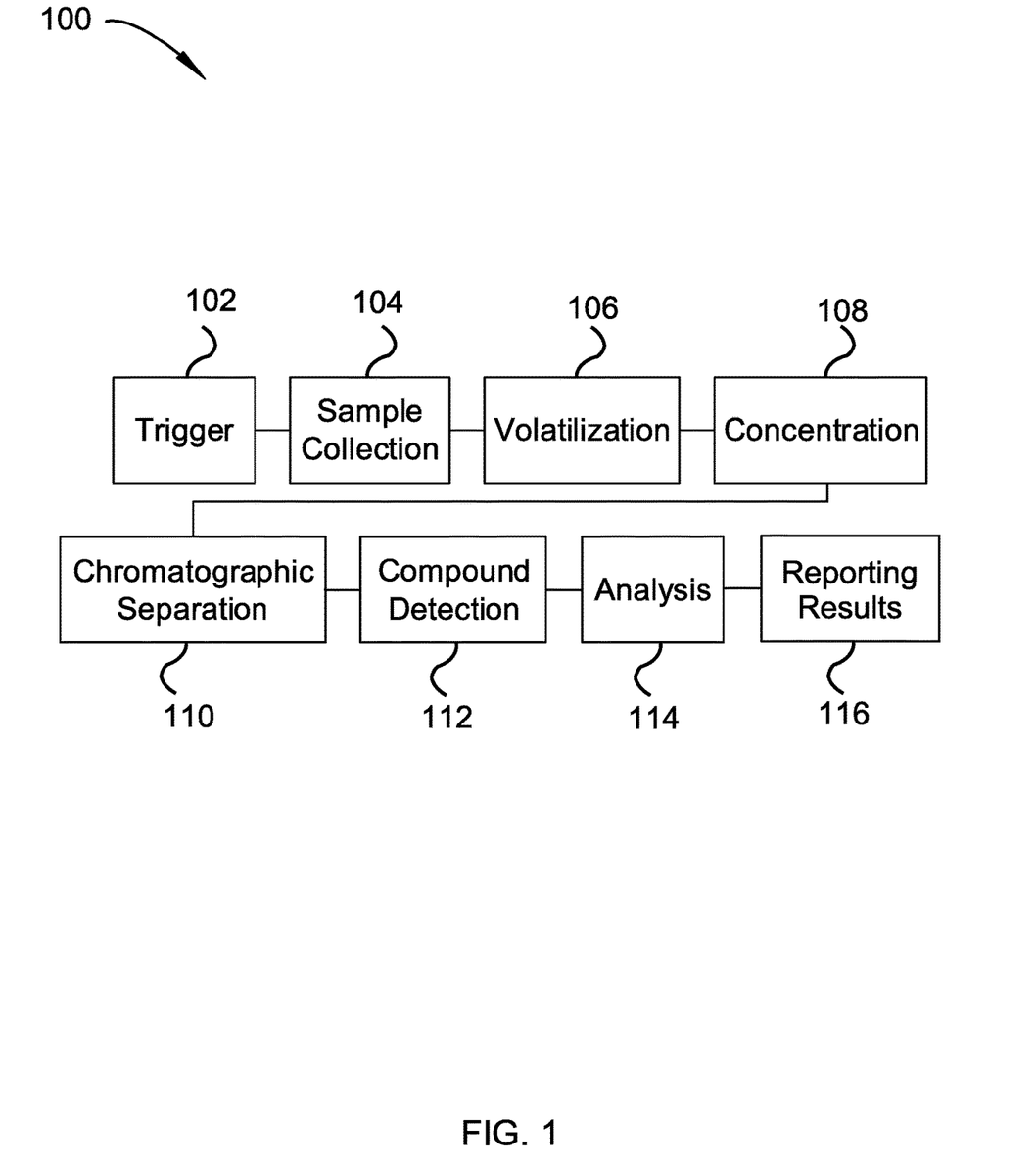
FIG. 1 shows a method for an in-toilet urinalysis system from trigger to analysis.

Referring to FIG. 1, method 100 portrays a trigger 102 that assesses the presence or non-presence of a sample and subsequently may trigger a sample collection 104. Trigger 102 may be a temperature sensor, force sensor, light sensor, motion sensor, camera, thermal imaging sensor, button, acoustic sensor, gas sensor, or a combination thereof. The sample collection 104 is followed by volatilization 106 of all or a portion of sample from sample collection 104. Volatilization 106 may be achieved in-part by heating a received sample 104. The heating may be a result of an optical light source of a measurement system used detect 112 and analyze 114 a received sample 104. A volatilized sample may then undergo concentration 108 followed by chromatographic separation 110. After the chromatographic separation 110 the sample may undergo compound detection 112 and analysis 114. Results of a chemical analysis of constituents in the volatilized sample 106 may be collected and stored locally and only remotely reported after a period of time such as 1, 2, 3, 6, or 12 months. Additionally, or alternatively, the collected and stored data may be reported to a remote database or healthcare database when a predetermined number of toilet samples have been collected. A predetermined number of samples may be 10, 30 50, or 100 or more toilet samples or toilet sessions of a specific toilet user. An identification of a toilet user may be stored in a user account associated with a specific toilet user as taught and described in a commonly owned US patent application titled "User Identifying Toilet Apparatus" application Ser. No. 15/150,797 which is hereby incorporated by reference in its entirety for all that it teaches.

Figure 2:
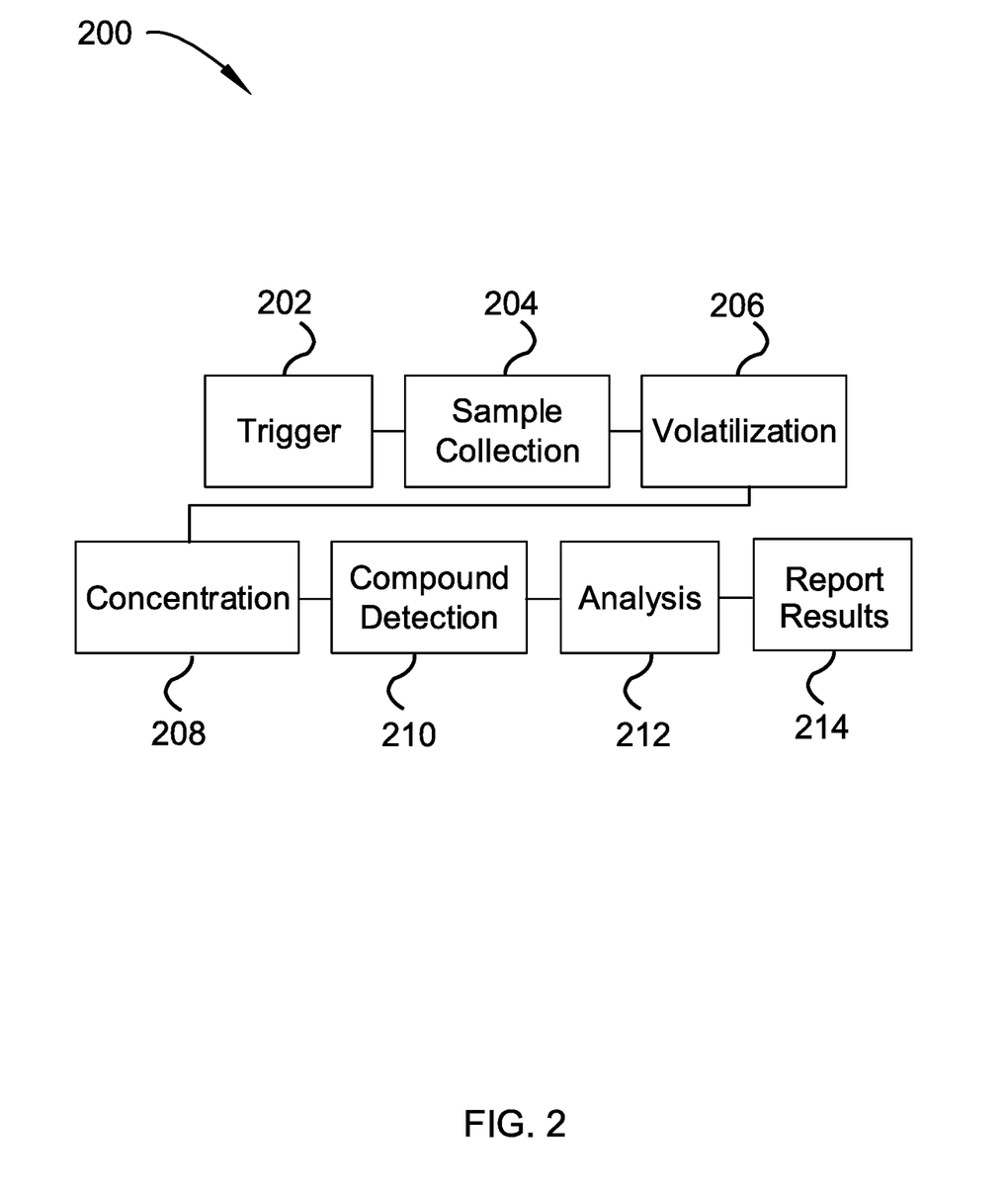
FIG. 2 shows a method for an in-toilet urinalysis system from trigger to analysis.

FIG. 2 shows method 200 with trigger 202 that assesses the presence or non-presence of a sample and subsequently may trigger a sample collection 204. Trigger 202 may be a temperature sensor, force sensor, light sensor, motion sensor, camera, thermal imaging sensor, button, acoustic sensor, gas sensor, or a combination thereof. The sample collection 204 is followed by volatilization 206 of all or a portion of a sample from sample collection 204. A volatilized sample may then undergo concentration 208, following which the sample may undergo compound detection 210 and analysis 212. Results of a chemical analysis of constituents in the volatilized sample 206 may be collected and stored locally and only remotely reported after a period of time such as 1, 2, 3, 6, or 12 months. Additionally, or alternatively, the collected and stored data may be reported to a remote database or health care database when a predetermined number of toilet samples have been collected. A predetermined may be 10, 30 50, or 100 or more toilet samples or toilet sessions of a specific toilet user. An identification of a toilet user may be stored in a user account associated with a specific toilet user as taught and described in a commonly owned US patent application titled "User Identifying Toilet Apparatus" application Ser. No. 15/150,797 which is hereby incorporated by reference in its entirety for all that it teaches.

Figure 3:
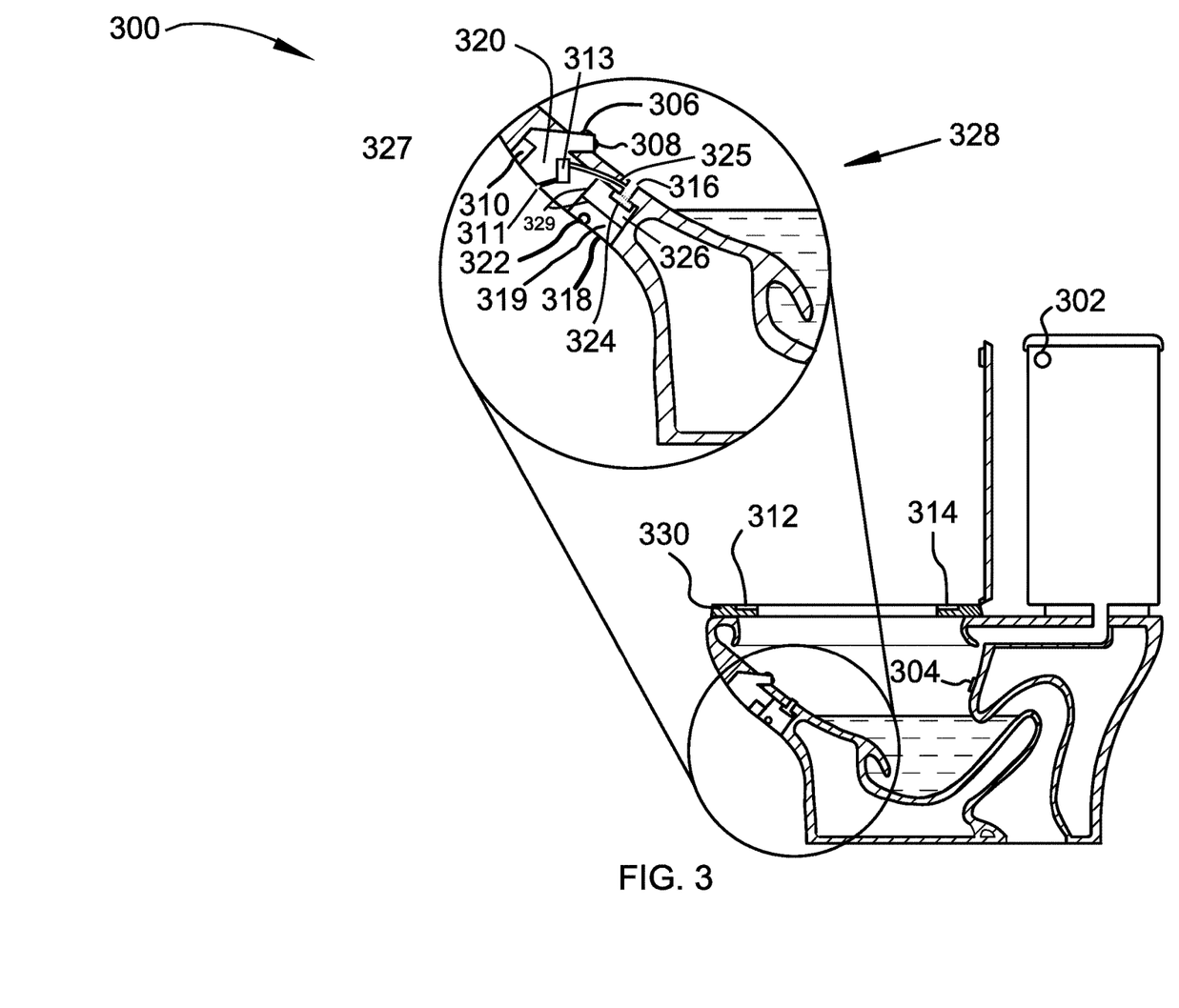
FIG. 3 shows a side view of a toilet with an in-toilet urinalysis system.

FIG. 3 shows an illustration of a toilet 300 with an in-toilet sampling and measuring system 328. The toilet 300 also comprises sensors 302, 304, 306, 308, 312, and 314 that may be used to trigger sample volatilization, collection, and measurement by the toilet sampling and measurement system 328. Sensors 302, 304, 306, 308, 312, and 314 may be temperature sensors, force sensors, light sensors, motion sensors, cameras, thermal imaging sensors, buttons, acoustic sensors, gas sensors, or combinations thereof. Sensor 302 may comprise a button, switch, latch, touchpad, temperature sensor, strain gages, weight sensors, force sensors, optical sensors, motion sensors, audio sensors, or other mechanism that a user could use to trigger sample collection. Sensor 302 may also be in a different location, such as on the side of the toilet 300, on a nearby wall, or on a wireless remote or user device that can wirelessly interact with communication device transceiver 310. Transceiver 310 may be a wireless transceiver such as Bluetooth, WiFi, ZigBee, SureFi, etc., or a wired transceiver such as a USB or an Ethernet wired network connection. Transceiver 310 may be used to communicate with the Internet, remote databases, remote computers, local networks, user devices such as smartphones, tablets, and Ipads. Sensors 312 and 314 may be pressure or strain sensors that may indicate the presence of a user on a toilet seat 330. Sensor 304 may trigger sample collection by means of an optical, temperature, acoustic, or motion sensor.

The in-toilet urinalysis system 328 comprises sample receptacle 316, which may comprise a depression 316, within a toilet bowl of toilet 300, accessible by a heater port 325, a VOC collection area 326, and/or a capillary, slot or other surface tension-based liquid capture feature. A urine sample may be directly (a direct urine stream into the receptacle) or indirectly (runoff from an inner surface of the toilet) captured when user of toilet 300 urinates in the toilet.

A volatilizer system 318 may comprise a sample receptacle 316, a vacuum generator 319, one or more measurement devices 320, VOC exhaust port 322, molecular sieve 324 and VOC sampling area 326. A urine sample may be volatilized as it is transferred from the sample receptacle 316 through a molecular sieve 324 while heated air is bubbled through port 325. The heated air bubbled through port 325 may be generated as a result of cooling an optical measurement system and/or processors of one or more measurement devices 320. The heated air may be used to keep sample receptacle 316 at a predetermined temperature such as body temperature or in a temperature range between 90 and 200 degrees Fahrenheit before or while volatilizing a urine sample. The volatilizer system 318 may comprise a bubbler, a heater, a liquid absorbing material with high gas permeability, a vacuum device, a heated gas flow, a concentrator, a pre-concentrator, or a combination thereof. The volatilizer system 318 may use gas heated by an optical system of one or more measurement devices 320 to assist in the volatilization process. Heated air or heated liquid or direct thermal transfer may transfer heat between measurement device 320 and volatilizer 318 to assist in the volatilization process. A volatilized sample may pass from volatilizer 318 directly to the one or more measurement devices 320 or directly from a concentrator or separator to one or more measurement devices 320. Measurement devices 320 may measure volatile organic compounds found on a surface of receptacle 316 or volatilizer 318 using optical interrogation means. A gas chromatography column, a micro gas chromatography column, a liquid chromatography column, a micro liquid chromatography column, an electrophoresis column, or a micro electrophoresis column may be used in conjunction with measurement devices 320 and/or voltatilizer 318.

A VOC sample area 326 may be used to concentrate VOCs. The VOCs may be concentrated using a concentrator that adsorbs or absorbs volatile compounds. One or more measurement devices 320 may directly optically interrogate VOCs through one or more common walls 329 between the VOC collection chamber 326 and the one or more measurement devices 320 or through one or more common walls 329 with the vacuum generator 319. The common walls 329 may be constructed of heat resistant material such as fused silica or quartz. The common walls 329 may comprise lenses or lens arrays such as micro-lens arrays. Heat generated by one or more of the measurement devices 320 may be used to assist in volatilizing the urine sample and/or keeping sample receptacle 316 between 90 and 200 degrees Fahrenheit.

A forced air heat exchange system 313 may draw in ambient air at intake port 311 and remove heat from one or more light sources and processors of one or more measurement devices 320 using a forced air blower heat exchange system 313. By bubbling warmed gas through port 325 while applying a vacuum with vacuum generator 319, urine VOCs in receptacle 316 are dissolved in the warmed gas and pulled downward through molecular sieve 324 and into VOC collection chamber 326. An additional heat source, such as an inductive heater, may be used to assist in removing concentrated VOCs from a concentrator which may be located within or near VOC collection chamber 326. Vacuum and heat may be applied to assist in removing volatile compounds from the urine sample and/or from the VOC concentrator material within VOC collection chamber 326.

A vacuum generator 319 may be used assist in the volatilization and collection of VOCs from the urine sample in sample receptacle 316. Vacuum generator may have an exhaust port 322 for releasing vacuum exhaust and allowing VOCs to vent on an outer surface of toilet 300. A VOC sample collector may be attached to exhaust port 322 for sampling and collection of VOCs for remote processing. A sample collector may include vacuum vials, tubes, hoses and container which are capable of transporting VOC samples. A canine may also be presented to exhaust port 322 to sample concentrated VOCs released from a urine sample in receptacle 316.

Receptacle 316 may contain one or more temperature sensors embedded within the receptacle for monitoring and controlling a temperature of a urine sample and/or preheating of the receptacle 316.

A three-way or four-way by-pass line may be implemented between port 325, port 311, with an additional ambient exhaust port and an additional input port (not shown) to control heated gas temperatures and gas flow released into urine receptacle 316.

A concentrator or pre-concentrator located within VOC collection area 326 may adsorb or absorb volatized urine VOCs. The concentrator or pre-concentrator may be heated by an inductive heater to release or purge VOC out of the concentrator material. The inductive heater may heat the concentrator or pre-concentrator to between 90 and 700 degrees Fahrenheit. One or more measurement devices 320 may comprise a means of measuring VOCs, which may comprise a refractometer, an acoustic resonator, a canine's olfactory gland, a mass spectrometer, a refractometer, a means of measuring light absorption, or an array of sensing elements. The one or more measurement devices 320 may also comprise a metal oxide (MOX) sensor, an electrochemical sensor, a mass spectrometer, an acoustic resonator, a refractometer, a spectrometer, a gas chromatograph, or a liquid chromatograph, urine analysis spectrometer and/or a urine analysis color change reagent measurement system. The one or more measurement devices 320 may further comprise a wireless connectivity function 310 that allows data to be reported to a computer, database, or a user device such as a smartphone, iPad, or tablet.

In one embodiment, a user may sit on toilet seat 330 to use toilet 300. As the user sits on seat 330, sensors 312 and/or 314 may sense a weight or force of the user's weight and start a VOC collection and detection process. Heat exchange system 313 may start preheating sample receptacle 316. Additionally, or alternatively, sensors 304 may detect a change in ambient light and/or a temperature change of urine entering toilet 300 and start a VOC collection and detection process.

Sampling and measurement system 328 may be removable from toilet 300 from an outside surface of toilet 300 for cleaning and maintenance purposes. A water line (not shown) may introduce clean process water into measurement devices 320 and/or into volatilizer 318. Process water supplied by the water line may be used for measurement processing, for cleaning, and for cooling of the measurement devices 320. The process water may be released into the toilet bowl after the water is used in the measurement devices 320 and volatilizer 318. A cleaning routine may be implemented after urine processing is complete to clean urine receptacle 316, volatilizer system 318 and the one or more measurement devices 320. A purge cycle, using inductive heating, may be used to heat VOC collection area 326 to temperatures between 200 to 700 Fahrenheit to release or desorb any stored VOCs in a concentrator material and/or to purge any VOCs out of the collection area 326.

Figure 4:
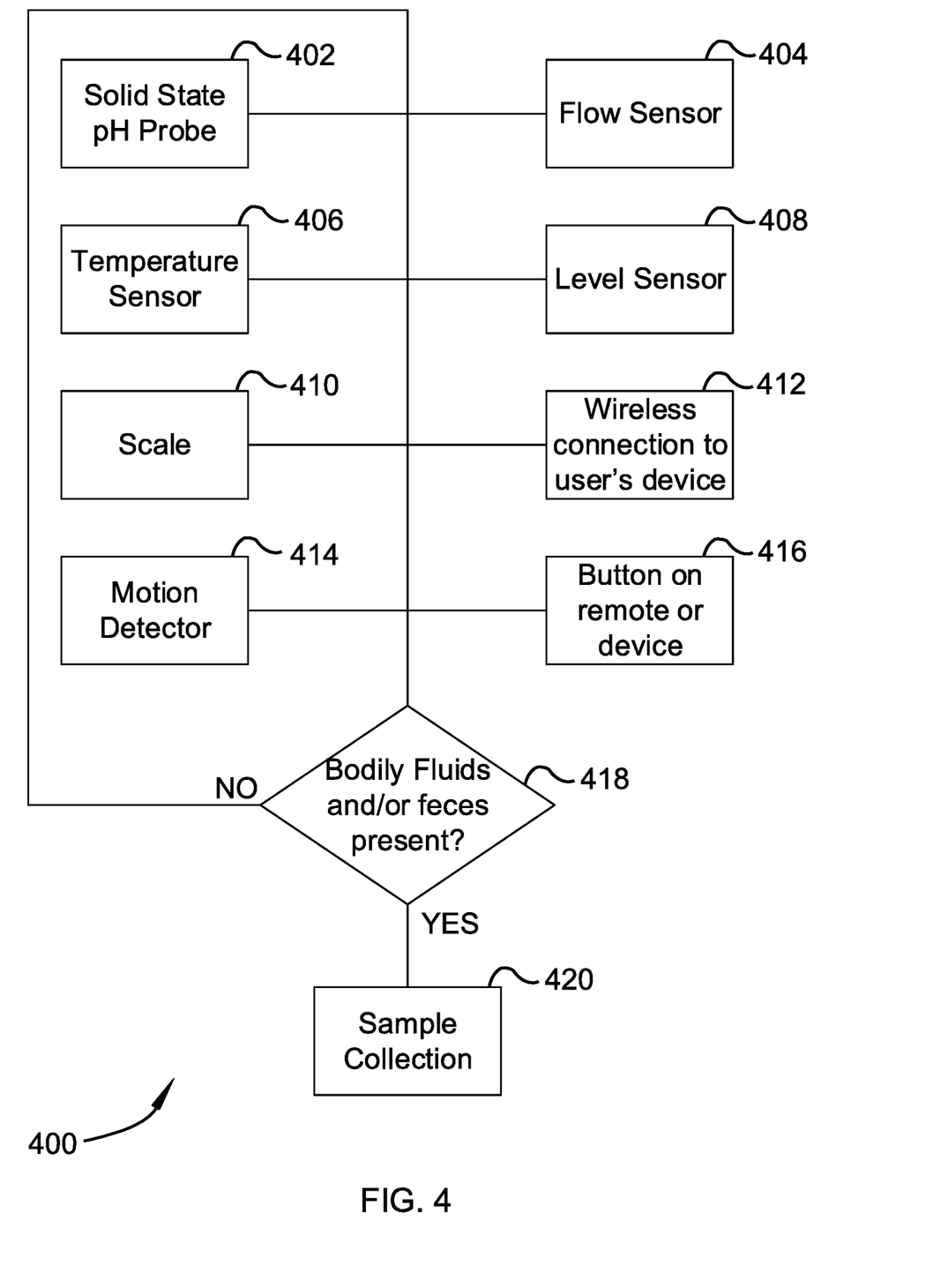
FIG. 4 is a method that takes input from a trigger or triggers and makes a decision based on said input.

FIG. 4 shows an array of potential triggering mechanisms and a method 400 for their use with an in-toilet urinalysis system. The triggering mechanisms may compromise a solid state pH probe 402, a flow sensor 404, a temperature sensor 406, a level sensor 408, a scale 410, a wireless connection to user's device 412, a motion detector 414, or a button 416. Additionally, any combination of this triggering mechanisms may be used in tandem to increase precision or efficiency. Input from the triggering mechanisms is used to verify presence of bodily fluids and/or feces. If the presence of bodily fluids and/or feces is verified, a decision 418 is triggered such that the method 400 will go on to a sample collection 420.

Figure 5:
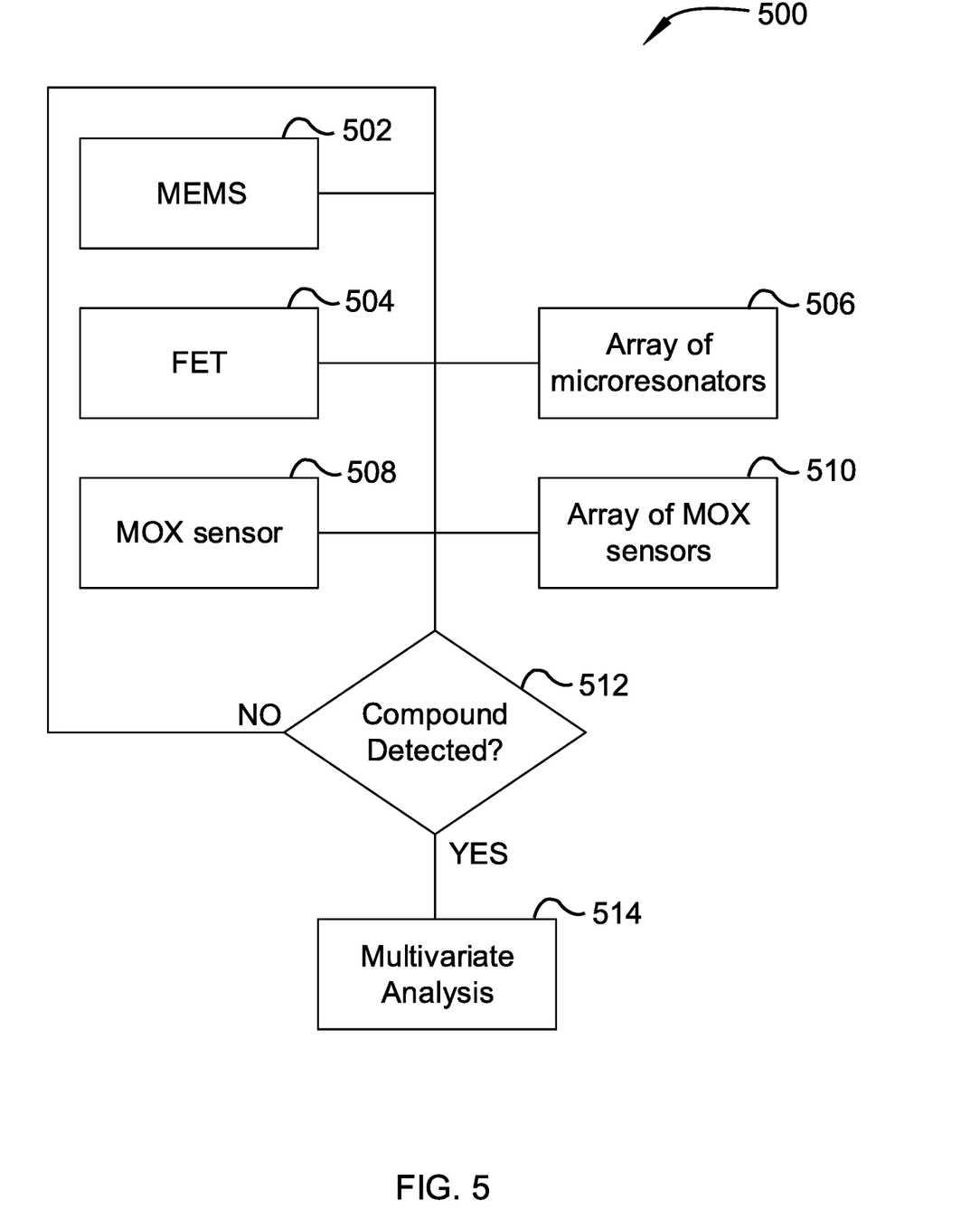
FIG. 5 is a method that takes input from a sensor or sensors and based on said input may trigger analysis of identified compounds.

FIG. 5 shows an array of sensors used to identify compounds present in a urinalysis and a method 500 for their use in an in-toilet urinalysis system. Compound detection 512 may be accomplished by means of any combination of the following: a microelectromechanical system 502, a field effect transistor 504, micro-resonators 506, a metal oxide sensor 508, or an array of metal oxide sensors 510. The metal oxide sensor 508 may also be an electrochemical sensor. Upon successful compound detection 512, a multivariate analysis 514 is triggered. Method 500 may take place in the one or more measurement devices 326 of FIG. 3.

Figure 6:
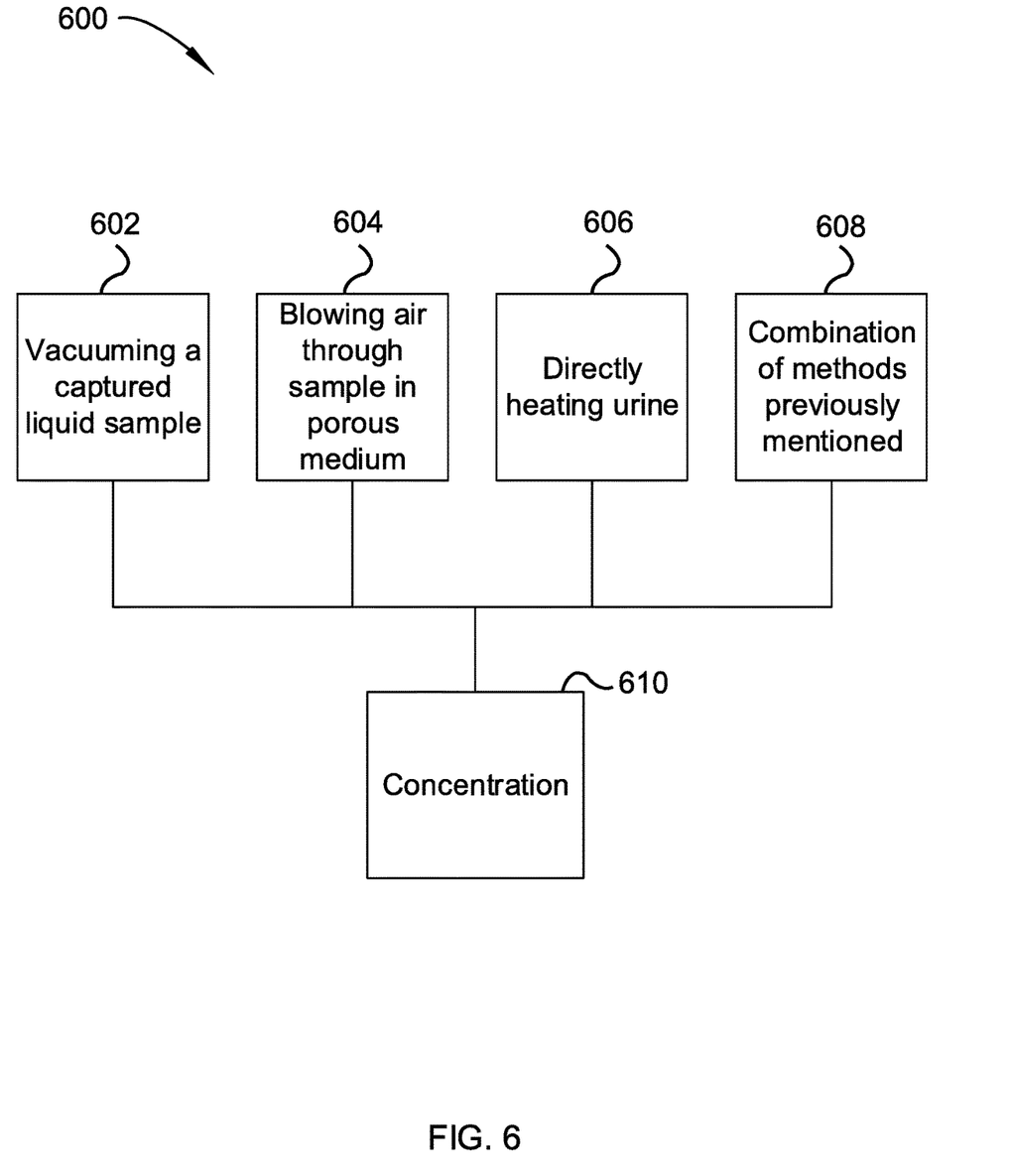
FIG. 6 is a variable method of sample volatilization and concentration.

FIG. 6 shows method 600, which specifies differing methods that may be used to achieve volatilization of a sample prior to concentration 610. Volatilization is used to draw out volatile organic compounds within the urine of a user. A volatilizer system may achieve volatilization by vacuuming a captured liquid sample 602, blowing gas or heated gas through a sample in a porous medium 604, directly heating urine 606, or any combination of previously stated methods 608.

Figure 7:
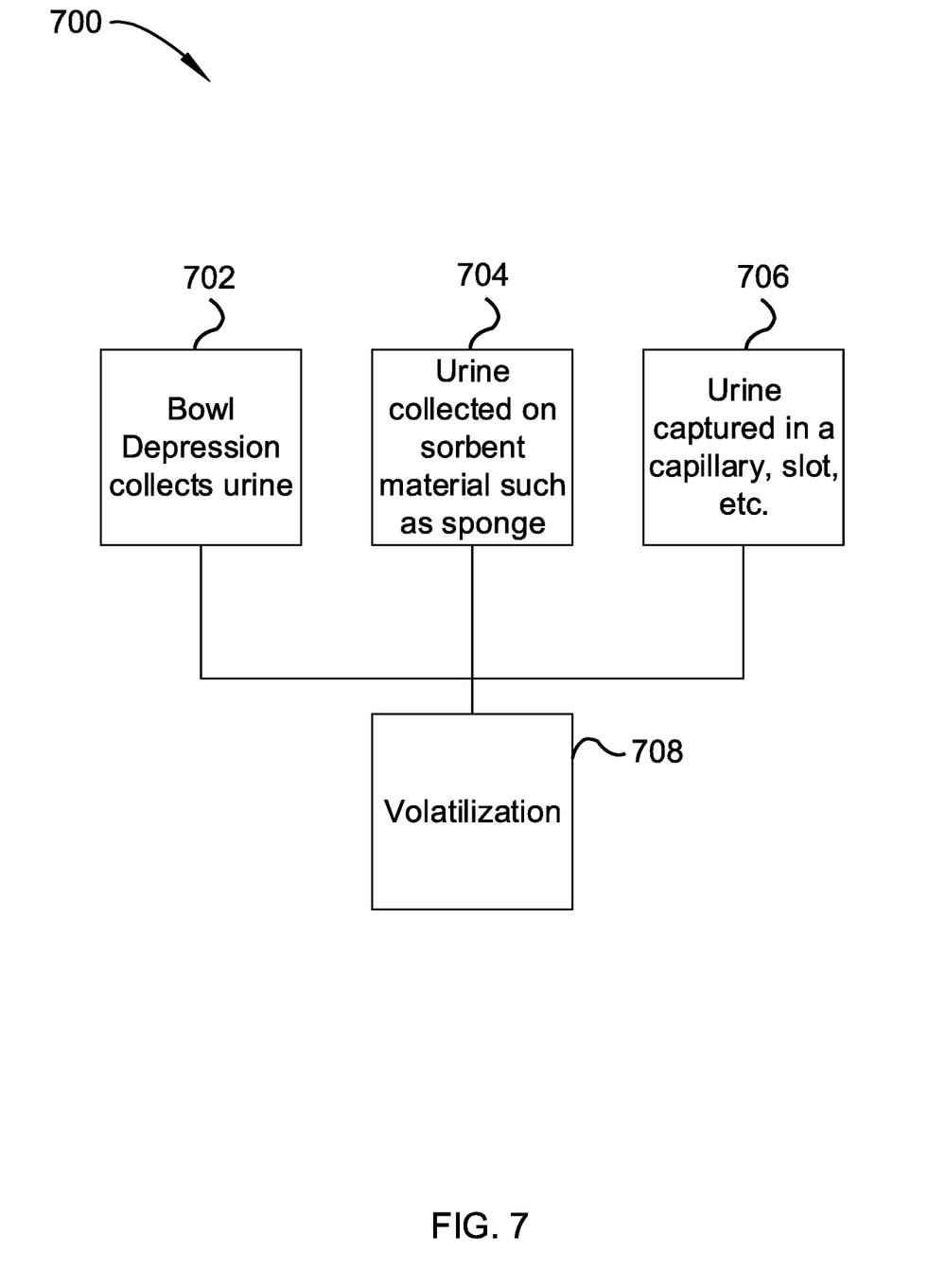
FIG. 7 is a variable method of sample collection and volatilization.

FIG. 7 shows a method 700 for sample collection prior to volatilization 708. Sample collection may be accomplished by a depression in a toilet bowl 702, urine collected onto a sorbent material 704, or urine captured in a capillary or slot 706. A bowl depression may include: a slit, a surface tension device, hydrophobic and hydrophilic coatings, an engineered surface such as a micro lens or micro lens array, and/or a molecular sieve.

Figure 8:
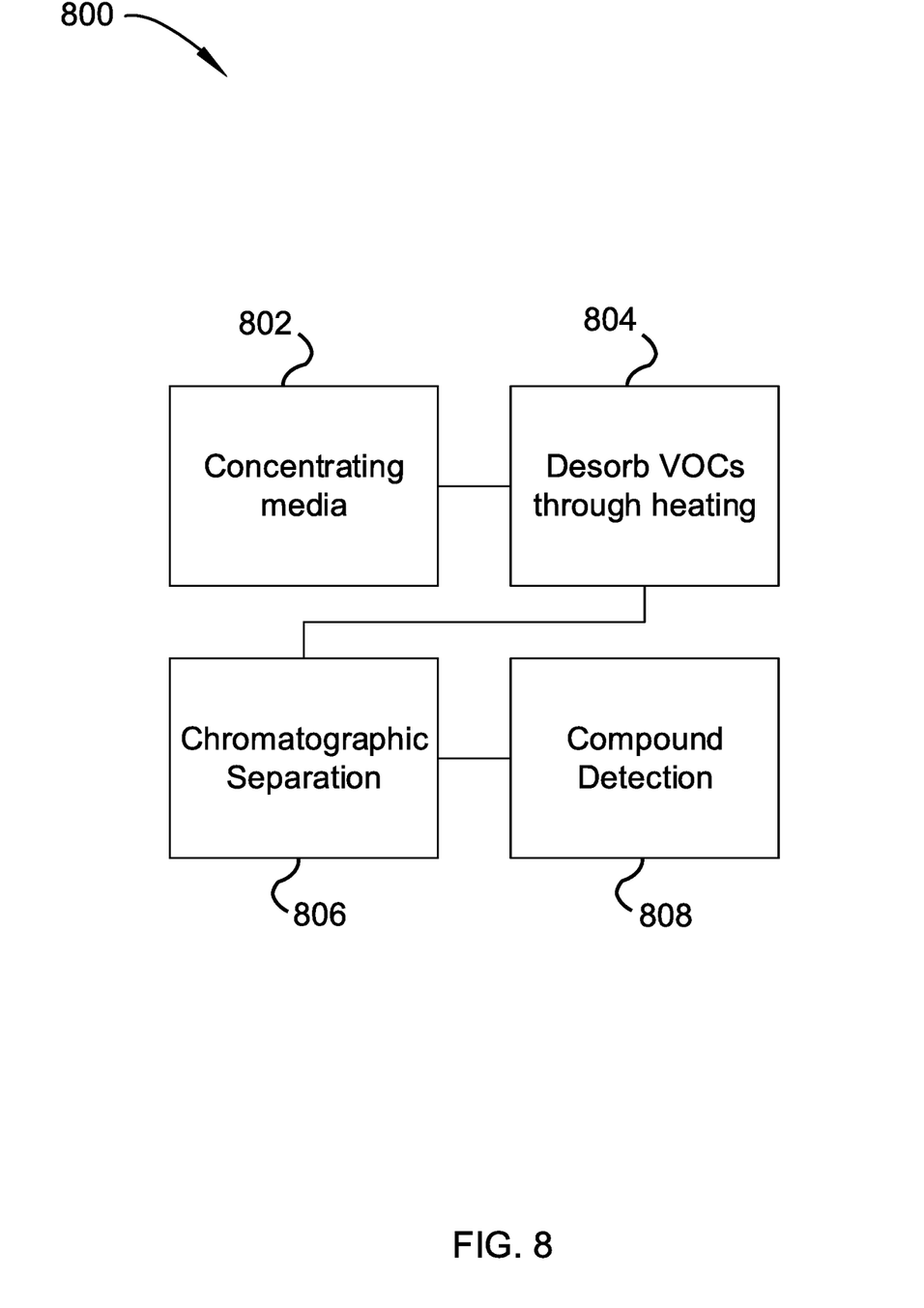
FIG. 8 is a method for an in-toilet urinalysis system from concentration to detection.

FIG. 8 shows a method 800 for taking a sample from media concentration 802 to compound detection 808. This is accomplished by means of VOC desorption by heating 804 followed by chromatographic separation 806. A purge or desorb cycle, using inductive heating, may be used to heat a VOC concentrating media 802 to temperatures between 100 to 700 Fahrenheit to release or desorb any stored VOCs in a concentrator material and/or to purge any VOCs out of the collection area 326. Compound detection 808 may be accomplished using on or more of: a metal oxide (MOX) sensor, an electrochemical sensor, a mass spectrometer, an acoustic resonator, a refractometer, a spectrometer, a gas chromatograph, or a liquid chromatograph, urine analysis spectrometer and/or a urine analysis color change reagent measurement system.

Figure 9:
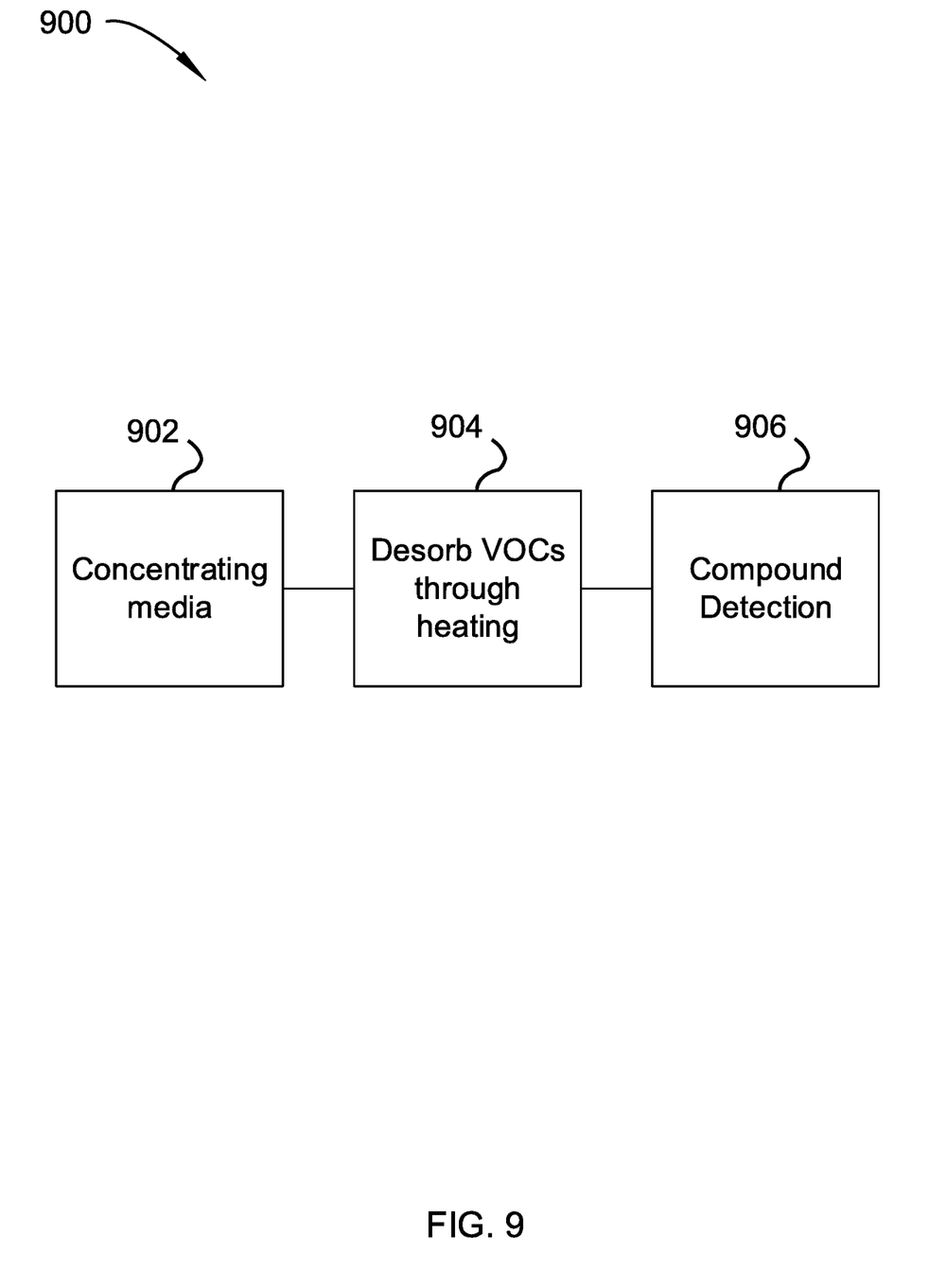
FIG. 9 is a method for an in-toilet urinalysis system from concentration to detection.

FIG. 9 shows a method 900 for taking a sample from media concentration 902 to compound detection 906. This is accomplished by means of VOC desorption by heating 904. Compound detection 906 may be accomplished using on or more of: a metal oxide (MOX) sensor, an electrochemical sensor, a mass spectrometer, an acoustic resonator, a refractometer, a spectrometer, a gas chromatograph, or a liquid chromatograph, urine analysis spectrometer and/or a urine analysis color change reagent measurement system.

Figure 10:
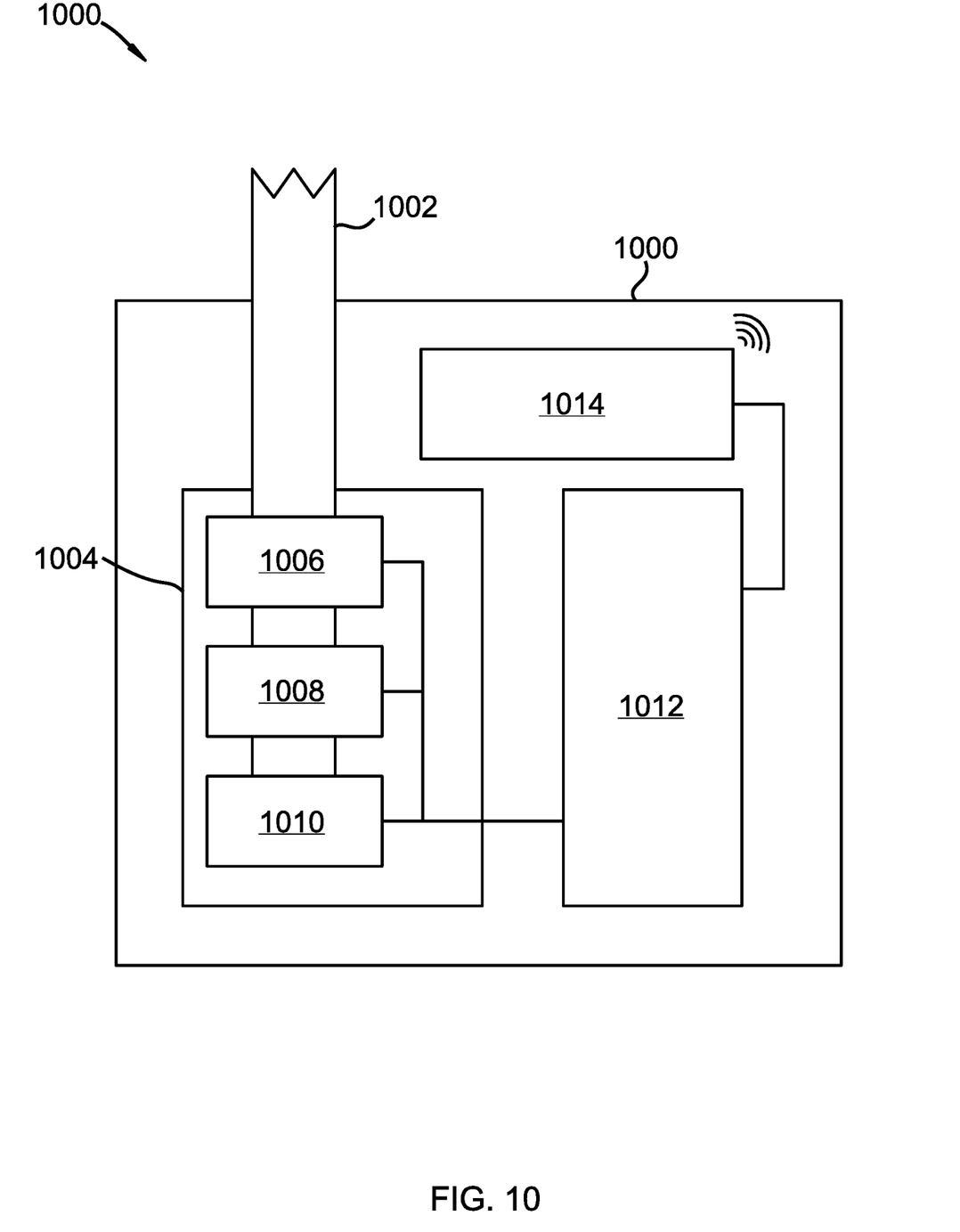
FIG. 10 is a block diagram of one or more measurement devices and related components.

FIG. 10 shows one or more measurement devices 1000 wherein VOCs are introduced via inlet 1002. Inlet 1002 may comprise a transfer mechanism, elution column, or other form of transfer. Devices 1006, 1008, and 1010 are used to detect VOCs received from the inlet 1002. The devices 1006, 1008, and 1010 may be any combination of sensors, systems, or devices used to identify various VOCs and chemical constituents associated therewith. Measure device array 1004 may comprise a liquid chromatography column, a micro liquid chromatography column, a gas chromatography column or a micro gas chromatography column. It is possible that more or less measurement devices than those shown are used to detect VOCs and chemical constituents. Data from the measurement devices 1006, 1008, and 1010 is transmitted to a processor 1012 which may analyze the data for the benefit of a user or forward the data to a database server for remote processing and analysis by way of transceiver 1014 through the Internet or local network. The analysis may then be transmitted to a computer, personal device, or database by means of wireless transmitter 1014 or through a remote Internet connection to a database server where the analysis took place.

The systems and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An in-toilet urinalysis system comprising:
a toilet bowl comprising a receptacle, wherein the receptacle is configured to receive a urine sample;
a urine volatilizer system, wherein the urine volatilizer system is attached to the toilet bowl and comprises a heater configured to generate heat, wherein the heat generated by the heater volatilizes at least a portion of the urine sample;
one or more measurement devices comprising a processor, wherein the one or more measurement devices include a light source or a processor that generates heat, measurement devices generate heat, wherein the one or more measurement devices is attached to the toilet bowl; and
a trigger sensor, wherein when the trigger sensor senses urination by a user, the trigger sensor actuates the one or more measurement devices causing the one or more measurement devices to conduct measurements of volatile organic compounds released from the urine sample followed by analysis of the measurements by the processor;
wherein the system is configured to remove heat from the light source or the processor to assist the urine volatilizer system in volatizing the urine sample.

2. The in-toilet urinalysis system of claim 1, further comprising a temperature sensor which measures a temperature of the urine sample, wherein the heater maintains the urine sample between 90 and 200 degrees Fahrenheit.

3. The in-toilet urinalysis system of claim 1, wherein the volatilizer system comprises: a liquid absorbing material with high gas permeability, a vacuum generator, or a bubbler.

4. The in-toilet urinalysis system of claim 1, further comprising a concentrator or pre-concentrator that adsorbs or absorbs the volatile organic compounds of the urine sample.

5. The in-toilet urinalysis system of claim 4, wherein the heater comprises an inductive heater which directly heats the concentrator or pre-concentrator.

6. The in-toilet urinalysis system of claim 1, further comprising a transceiver, wherein the measurements of volatile organic compounds collected by the one or more measurement devices are locally stored and the transceiver transmits the plurality of measurements to a remote device only after a user uses the toilet 10 times.

7. The in-toilet urinalysis system of claim 5, wherein the heater heats the concentrator or pre-concentrator to a temperature of between 90 to 700 degrees Fahrenheit.

8. The in-toilet urinalysis system of claim 1, wherein the one or more measurement devices include one or more of: a metal oxide (MOX) sensor, an electrochemical sensor, a mass spectrometer, an acoustic resonator, a refractometer, a spectrometer, a gas chromatograph, or a liquid chromatograph.

9. The in-toilet urinalysis system of claim 1, wherein the trigger sensor is one or more of: a temperature sensor, a force sensor, a light sensor, a pH sensor, a motion sensor, a camera, a thermal imaging sensor, a button, an acoustic sensor, or a gas sensor.

10. The in-toilet urinalysis system of claim 1, further comprising a transceiver, wherein the measurements of volatile organic compounds collected by the one or more measurement devices are locally stored and the transceiver transmits measurement trends to a remote device only after a user uses the toilet 10 times.

11. The in-toilet urinalysis system of claim 1, further comprising a transceiver, wherein the measurements of volatile organic compounds collected by the one or more measurement devices are locally stored and the transceiver transmits measurement trends to a remote device only after a user uses the toilet 30 times.

12. The in-toilet urinalysis system of claim 1, wherein the volatile organic compounds include one or more of: alcohols, ketones, alkanes, alkenes, aldehydes, carboxylic acids, ethers, pyrroles, nitriles, or aromatics.

13. The in-toilet urinalysis system of claim 1, further comprising an exhaust port which exhausts volatile organic compounds after measurement is complete.

14. The in-toilet urinalysis system of claim 1, wherein the one or more measurement devices comprise an array of sensing elements.

15. The in-toilet urinalysis system of claim 13, wherein the exhaust port is located on an exterior surface of the toilet such that a canine olfactory gland or a removable collection device is configured to access the exhaust port.

16. The in-toilet urinalysis system of claim 1, wherein the one or more measurement devices comprise a liquid chromatography column, a micro liquid chromatography column, a gas chromatography column or a micro gas chromatography column.

17. The in-toilet urinalysis system of claim 1, wherein the one or more measurement devices comprise a urine analysis spectrometer.

18. The in-toilet urinalysis system of claim 1, further comprising a transceiver, wherein the transceiver transmits the measurements collected by the one or more measurement devices to a cloud based medical health system each time a toilet user urinates in the toilet bowl.

19. An in-toilet urinalysis system comprising:
a toilet bowl comprising a receptacle, wherein the receptacle is configured to receive a urine sample;
a urine volatilizer system, wherein the urine volatilizer system is attached to the toilet bowl and comprises a heater configured to generate heat, wherein the heat generated by the heater volatilizes at least a portion of the urine sample;
an electrophoresis column or a micro electrophoresis column comprising a processor, wherein the electrophoresis column or the micro electrophoresis column generates heat, wherein the electrophoresis column or micro electrophoresis column is attached to the toilet bowl;
a trigger sensor, wherein when the trigger sensor senses urination by a user, the trigger sensor that actuates the electrophoresis column or the micro electrophoresis column causing the electrophoresis column or the micro electrophoresis column to conduct measurements of volatile organic compounds released from the urine sample followed by analysis of the measurements by the processor; and
wherein the heat generated from the electrophoresis column or the micro electrophoresis column is used in a heat exchange system to provide heat to the urine volatilizer system for volatizing the urine sample.

\* \* \* \* \*